(12) United States Patent
Wallenstein et al.

(10) Patent No.: US 8,118,847 B2
(45) Date of Patent: Feb. 21, 2012

(54) ANTERIOR VERTEBRAL PLATE WITH UNDERSIDE LOCKING MECHANISM

(75) Inventors: Todd M. Wallenstein, Ashburn, VA (US); Peter M. Harris, Leesburg, VA (US); Josef E. Gorek, Ross, CA (US); Jean-Jacques Abitbol, San Diego, CA (US); Gil Tepper, Beverly Hills, CA (US)

(73) Assignee: K2M, Inc., Leesburg, VA (US)

( * ) Notice: Subject to any disclaimer, the term of this patent is extended or adjusted under 35 U.S.C. 154(b) by 465 days.

(21) Appl. No.: 11/368,521

(22) Filed: Mar. 7, 2006

(65) Prior Publication Data

US 2007/0043369 A1    Feb. 22, 2007

(51) Int. Cl.
*A61B 17/80* (2006.01)

(52) U.S. Cl. .................................. 606/286; 606/289

(58) Field of Classification Search ............. 606/61, 606/70, 71, 289, 293
See application file for complete search history.

(56) References Cited

U.S. PATENT DOCUMENTS

| 4,503,848 | A | * | 3/1985 | Caspar et al. | 606/280 |
|---|---|---|---|---|---|
| 5,151,103 | A | * | 9/1992 | Tepic et al. | 606/291 |
| 5,549,612 | A | * | 8/1996 | Yapp et al. | 606/293 |
| 6,416,528 | B1 | * | 7/2002 | Michelson | 606/185 |
| 7,322,984 | B2 | * | 1/2008 | Doubler et al. | 606/70 |
| 7,438,715 | B2 | * | 10/2008 | Doubler et al. | 606/71 |
| 2002/0147450 | A1 | * | 10/2002 | LeHuec et al. | 606/61 |
| 2003/0018335 | A1 | * | 1/2003 | Michelson | 606/61 |
| 2003/0060828 | A1 | * | 3/2003 | Michelson | 606/71 |
| 2003/0187440 | A1 | * | 10/2003 | Richelsoph et al. | 606/61 |
| 2003/0212399 | A1 | * | 11/2003 | Dinh et al. | 606/61 |
| 2004/0127899 | A1 | * | 7/2004 | Konieczynski et al. | 606/69 |
| 2005/0049593 | A1 | * | 3/2005 | Duong et al. | 606/69 |
| 2005/0075633 | A1 | * | 4/2005 | Ross | 606/61 |
| 2006/0085000 | A1 | * | 4/2006 | Mohr et al. | 606/69 |
| 2006/0116683 | A1 | * | 6/2006 | Barrall et al. | 606/71 |
| 2006/0122607 | A1 | * | 6/2006 | Kolb | 606/71 |
| 2006/0155285 | A1 | * | 7/2006 | Anderson | 606/70 |

* cited by examiner

*Primary Examiner* — Nicholas Woodall (74) *Attorney, Agent, or Firm* — Carter, DeLuca, Farrell & Schmidt, LLP (57) ABSTRACT

Provided is a device, system, and method for the fixation of the spine. In particular, the present invention provides a system that includes a low profile anterior vertebral plate and screws for fixation and stabilization of the cervical spine, the anterior vertebral plate having a selectable locking mechanism embedded in the underside of the plate during the manufacturing thereof and providing a visual locked indicator on the top side of the plate.

14 Claims, 12 Drawing Sheets

ANTERIOR VERTEBRAL PLATE WITH UNDERSIDE LOCKING MECHANISM

BACKGROUND OF THE INVENTION

1. Field of the Invention

The present invention relates to devices, systems, and methods for the fixation of the spine. In particular, the present invention relates to a system that provides a low profile anterior vertebral plate and screws for fixation and stabilization of the cervical spine, the anterior cervical plate having a selectable screw locking mechanism embedded in the under side of the plate during the manufacturing thereof and providing a visual locked indicator on the top side of the plate.

2. Background of the Technology

Disease, the effects of aging, or physical trauma resulting in damage to the spine has been treated in many instances by fixation or stabilization of vertebra. The use of plates and screws for fixation and stabilization of the cervical vertebra has been widely accepted as a reliable practice and has proven to be highly successful clinically.

The various plates, which are attached to the anterior vertebral bodies of the spinal column by bone screws have some common features such as relatively flat body profiles that define multiple holes or slots through which the screws fit and are threaded into the bone. Among the differences between the conventionally used plates and screws is the manner in which the screws are locked into place in the hole or slot of the plate after the screws have been secured to the bone.

These conventional devices can be generally grouped into three basic categories with regard to how the screws are captured or secured in the plates.

The earliest plate designs can be categorized as Group I type plates. These simple designs were standard bone plates having holes through which screws were passed and screwed into the bone. These plates had no special provision for attaching the screws to the plate and as such were susceptible to having the screws back out of the plate over time. Unfortunately, there have been clinically reported instances of screws backing out of these simple Group 1 type plates with resulting surgical complications. Due to the generally unreliable nature of Group 1 type plates, fixation of the screw to the bone and to the plate is now considered as a basic requirement for vertebral plates. Due to the lack of predictable security of the screw to the plate, Group 1 type plates have fallen out of favor and have virtually disappeared from the market.

Recently efforts have been made in two generally different ways to provide features in the plates which are specifically designed to hold the screws in position once they have been inserted through the plate and screwed into the bone. One direction taken in this effort has been to design plates that incorporate retaining rings or snap features in the plates, which are configured to hold the inserted screw in place. These Group 2 type plates are very common and widely used; however, an inherent problem associated with such plates is the use of the additional very small retaining elements which can become disengaged from the plate and migrate into the surrounding soft tissues. The use of such small additional locking elements to the plates have also made it difficult to determine if the locking feature has properly engaged the screw in a locked position. Further, the difficulty experienced in accessing and disengaging the small locking elements and removing the screws from a Group 2 type plate has caused some concern for the continued use of such plates.

The other direction taken in this effort to provide plates with locking elements can be categorized as the Group 3 type plates. Group 3 type plates all provide dedicated overlying features, which are attached to plates for the purpose of covering at least a portion of the screw and thereby holding the screws in a seated and locked position. Generally Group 3 type plates are designed to provide a variety of screw covering plates, which can be selectively slid or rotated into position over at least a portion of the screw head to prevent the screw from backing out once it has been inserted. Group 3 type plates also include those mechanisms located on the top side of the plate that bear against the screw. Another less sophisticated, yet still overlying type locking mechanism, includes those plates wherein the screw is threaded through the plate in an effort to secure the screw from easily backing out. Such threaded plates simply rely on the threaded portion of the plate hole or slot to overlay the threaded portion of the screw as a locking means.

The Group 3 type plates typically require an increase in the overall composite thickness of the plate in order to accommodate the additional locking feature attached to the top side of the plate. This is a particularly unacceptable condition due to the use of such plates in an area of the spine where a thinner profile for the plate assembly is preferred. Another major problem with the Group 3 type plates is that the overlying locking element cannot always be properly positioned over the screw head if the screw was, due to anatomical necessity, positioned through the plate and into the bone at an angle such that the screw head does not fully seat in the screw recess provided on the top side of the plate. Further, if one of the overlying locking elements of a Group 3 type plate should loosen or become disengaged it is free to float loose from the top side of the plate and migrate into the surrounding soft tissue. Those simpler designs which rely only on the overlying threads of the threaded plate hole or slot to hold the screw in place are particularly difficult to use clinically in that they must be simultaneously threaded into the bone and the plate but with varying pitches and, as such, have not proven successful.

There is therefore, an unfulfilled need for a anterior cervical plate system that can maintain a relatively low profile, as found in the non-locking plates while providing the security of a locking plate system and doing so no matter how angulated the inserted screw may be. Further, there is a need for a vertebral plate that does not have the attachment of added locking elements to the top side of the plate with the predictable problems of locking elements becoming disengaged from the plate and migrating away from the top side of the plate into the surrounding soft tissue.

SUMMARY OF THE INVENTION

The present invention meets the above identified need by providing an anterior vertebra plate device and system for aligning and fixing vertebral bodies.

It is an object of the present invention to provide an anterior vertebral fixation plate with an integral, selectable screw locking element embedded in the under side, bone-facing surface of the plate.

It is further an object of the present invention to provide a low profile anterior vertebral plate for fixation and stabilization of the cervical spine, the anterior cervical plate having an integral, selectable locking mechanism embedded in the underside of plate for holding screws securely in position relative to the plate.

It is further an object of the present invention to provide an anterior vertebral plate having a factory-installed complete locking mechanism.

It is further an object of the present invention to provide an anterior vertebral plate having a locking mechanism embedded in the underside of the plate wherein all elements of the plate and locking mechanism are assembled during the manufacturing process prior to use thereof in a surgical procedure.

It is further an object of the present invention to provide an anterior vertebral plate having a locking mechanism embedded in the under side of the plate with a lock actuating element and a locking element position indicator provided on the top side of the plate.

It is further an object of the present invention to provide an anterior vertebral plate having a locking mechanism that fully locks angularly inserted screws into position in the plate.

It is further an object of the present invention to provide an alternative embodiment of the anterior vertebral plate having multiple strategically positioned feet for interfacing between the underside of the vertebral plate body and the underlying screw-attached bone.

It is further an object of the present invention to provide a system for use in the fixation of vertebrae, wherein the system includes an anterior vertebral plate having an integral, factory-assembled locking mechanism embedded in the under side of the plate and a set of bone screws configured to pass through the plate and attach to bone.

It is further an object of the present invention to provide a system for use in the fixation of vertebrae, wherein the system can be static or dynamic.

It is further an object of the present invention to provide a method for the fixation of vertebra, wherein the method includes the attachment of an anterior vertebral plate to the underlying bone using bone screws, the vertebral plate having an integral, factory-installed locking mechanism embedded in the underside of the plate.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Detailed embodiments of the present invention are disclosed herein; however, it is understood that the following description and accompanying FIGS. 1A-C to FIG. 14 are provided as being exemplary of the invention, which may be embodied in various forms without departing from the scope of the claimed invention. Thus, the specific structural and functional details provided in the description of present invention are non-limiting, but serve merely as a basis for the invention as defined by the claims provided herewith. The device described below can be modified as needed to conform to further development and improvement of materials without departing from concept of the invention.

The present invention, as shown in FIGS. 1A-C to FIG. 14 provides a a vertebral plate system, generally shown at 10 that includes a vertebral plate 12 and bone screws 22 for fixation of the vertebral plate 12 to underlying bone. The vertebral plate system 10 can be employed to fix one or multiple vertebral levels.

Figures 8A, 8B, 8C:
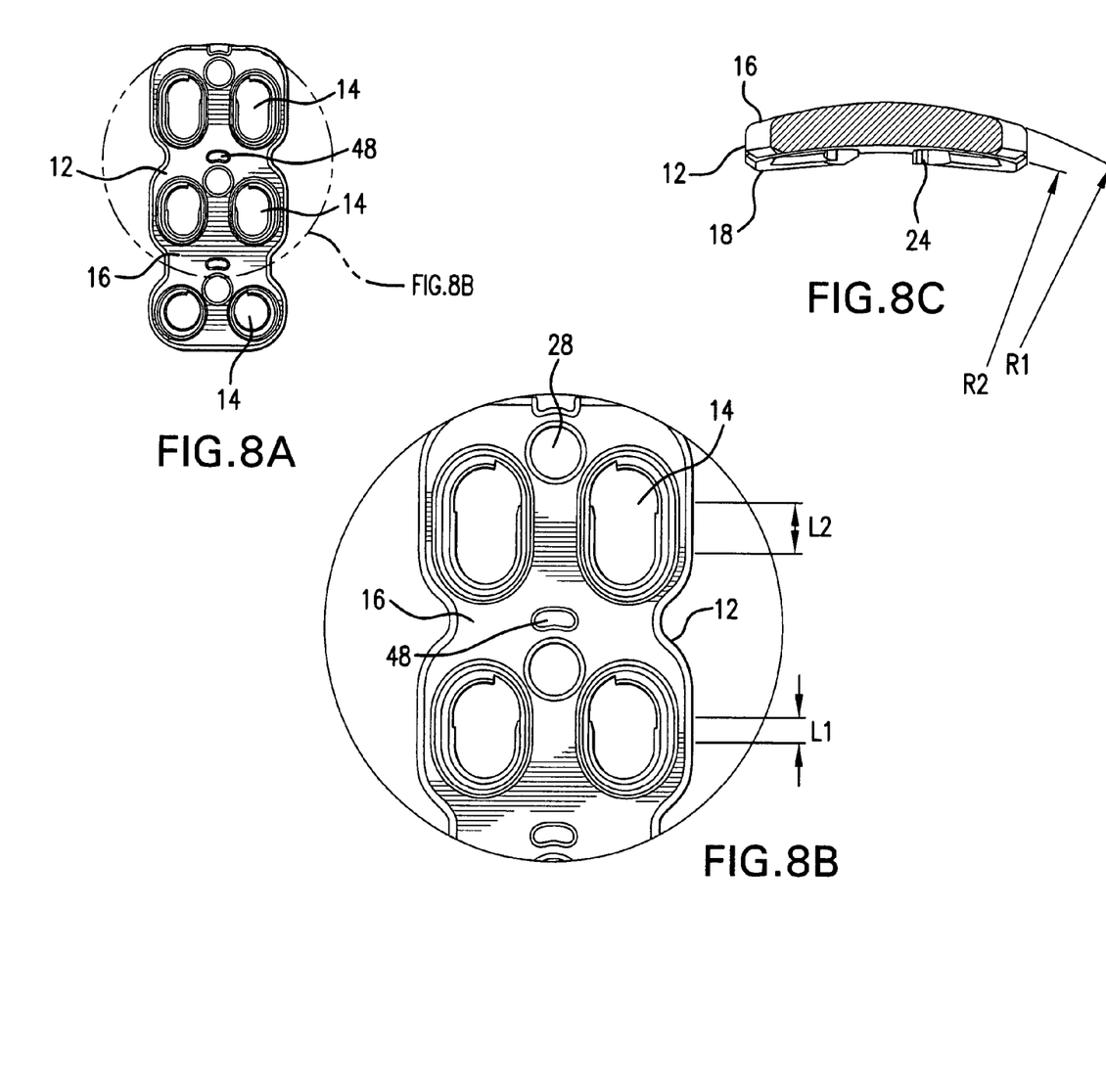
FIGS. 8A-C respectively show a top, magnified detail, and top cross-sectional view of a 2-level embodiment of the vertebral plate according to the present invention.
Figure 9A:
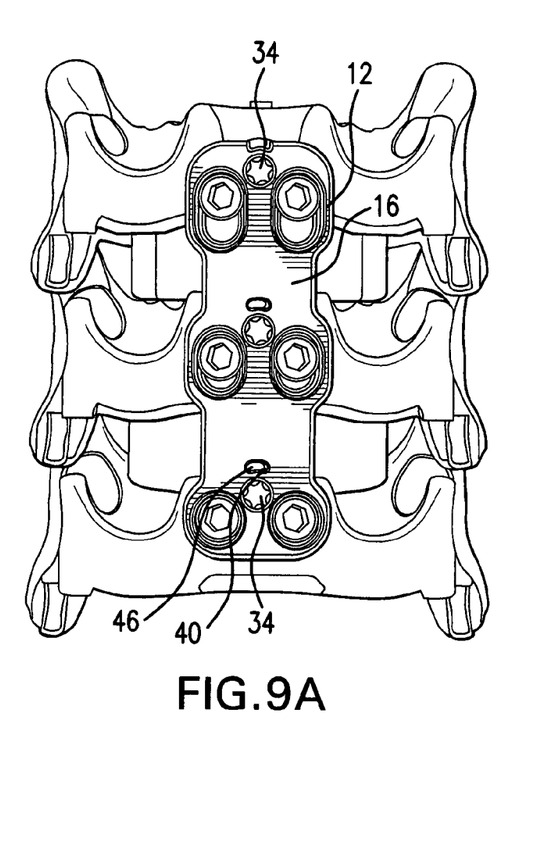
FIGS. 9A-F respectively show in FIG. 9A a 2-level embodiment of the present invention secured to a spine, in FIG. 9B the vertebral plate shown in FIG. 9A without bone screws and disassociated from the spine, in FIGS. 9C-F different perspectives of the locking mechanism including a cross-sectional view in FIG. 9F.
Figure 9B:
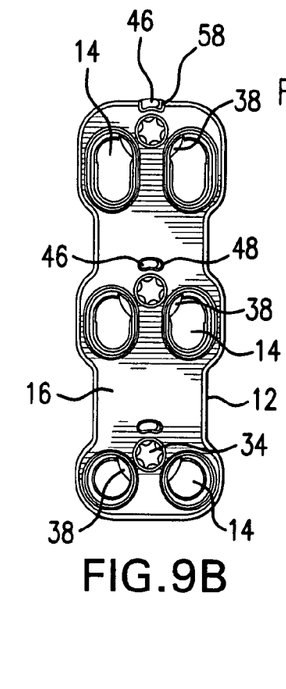
Figure 9C:
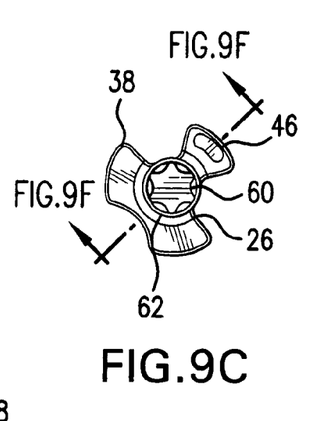
Figure 9D:
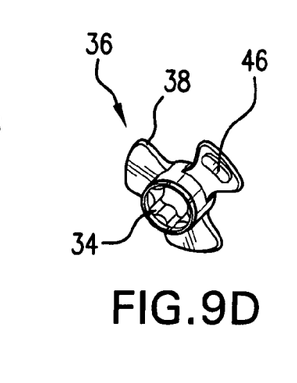
Figure 9E:
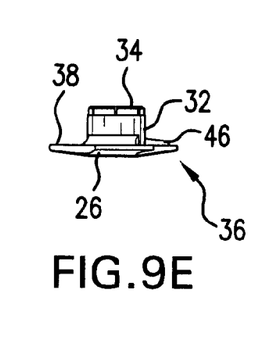
Figure 9F:
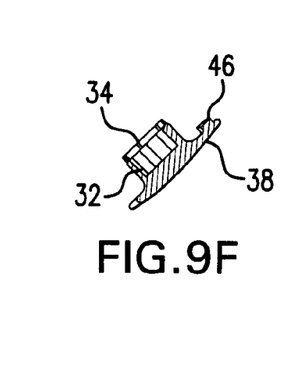

The vertebral plate 12 can be substantially planar or contoured in either or both the cephalad/caudal and/or medial/lateral planes. As shown in FIG. 8C, the top side 16 and the underside 18 of the vertebral plate 12 can both be configured with concave contours having the same or different radii of curvature. The vertebral plate 12 defines at least two bone screw portals 14, such as holes or slots, that provide a through passage that communicates from the top side 16 of the vertebral plate 12 through to the underside 18 of the vertebral plate 12. The at least two bone screw portals 14 are sized and configured to permit the passage of the shank portion 20 of each of a corresponding bone fixation element, which are preferably bone screws 22.

As best shown in FIGS. 1A-C, 2A-C, 3A-C and 10, the vertebral plate 12 plate, in addition to the at least two bone screw portals 14, defines at least one generally circular shaped lock recess 24 in the underside 18 of the vertebral plate 12. The lock recess 24 is sized and configured to accept a rotatable locking mechanism 36. The axial or central portion of the generally circular lock recess 24 defines a lock shaft passage 28 that provides a through passage from the lock recess 24 on the underside 18 of the vertebral plate 12 through to the driving element recess 30 defined in the surface of the top side 16 of the vertebral plate 12. The rotatable locking mechanism 36 is sized to fit within the lock recess without the base portion 26 of the locking mechanism 36 extending beneath the surface plane of the underside of the vertebral plate 12. The base portion 26 of the locking mechanism 36 supports an integral upward extending lock operating shaft 32, which extends through the lock shaft passage 28 of the vertebral plate 12 and terminates as a lock driving element 34 that is rotatably secured in the driving element recess 30. The upper reach of the lock driving element 34 is to a position slightly exposed on the surface plane of the top side 16 of the vertebral plate 12, thus providing a vertebral plate with the smoothest possible top side surface for contact with adjacent soft tissues.

Figure 10:
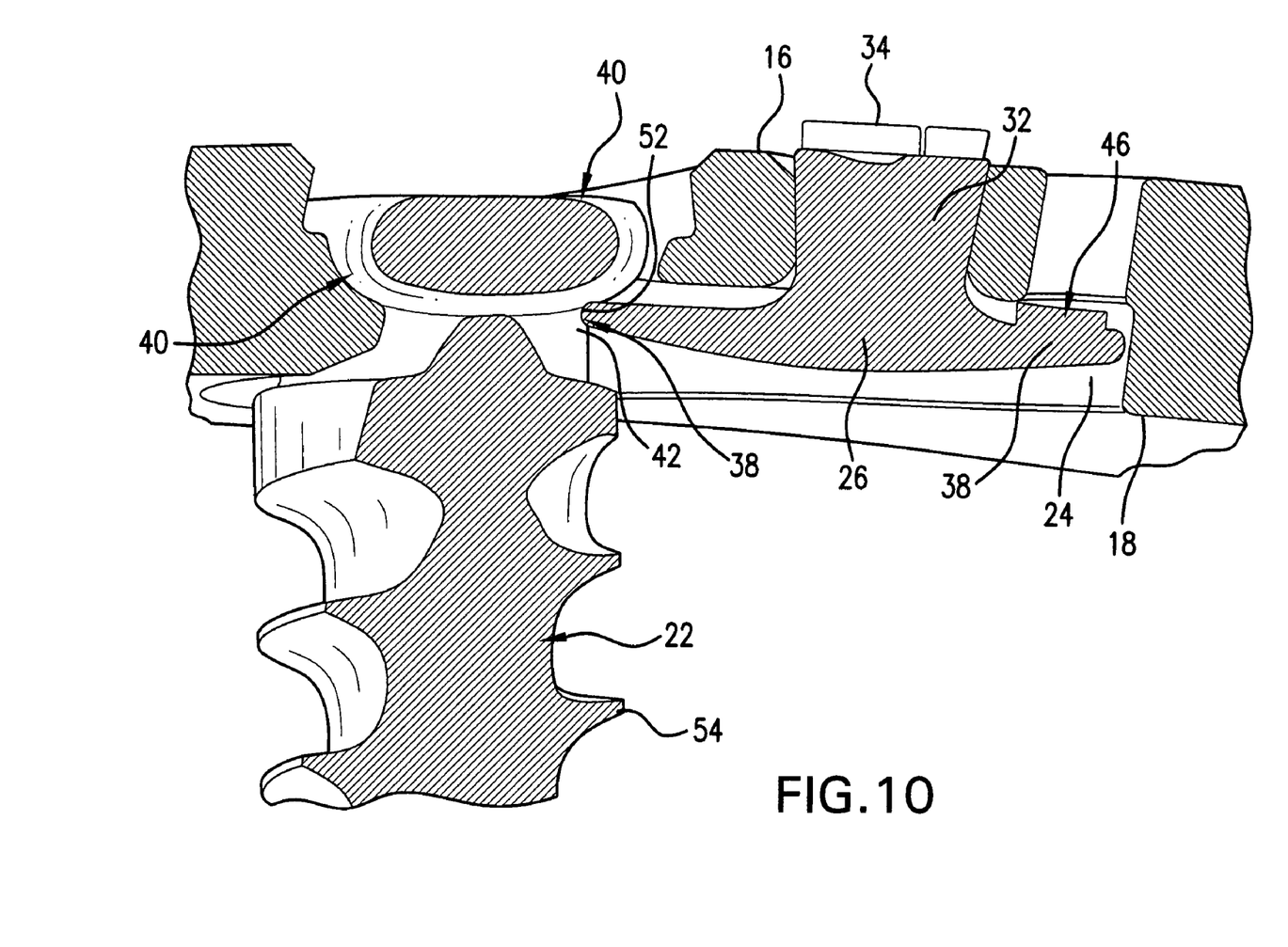
FIG. 10 shows a cross-sectional view of the portion of the vertebral plate defining the bone screw receiving portal with a bone screw positioned therein and secured by the locking mechanism according to the present invention.

As best shown in FIG. 10, the base portion 26, its integral lock operating shaft 32, and its integral lock driving element 34 are respectively contained and freely rotatable within the continuous passage formed by the respective interconnected lock recess 24, the lock shaft passage 28, and the driving element recess 30. This assembly thus rotatably positioned and embedded within the dedicated recesses of the underside 18 of the vertebral plate 12 provides a locking mechanism as generally shown at 36. The generally circular configuration of the base portion 26 of the locking mechanism 36 is punctuated by locking portions or flanges 38 which project radially from the central axis of the lock operating shaft 32 and serve to interact with the bone screws 22 when the lock driving element 34 is manually moved so as to rotate the flanges 38 of the base portion 26 into a locked position with one or more adjacently located bone screws 22. When in a locked position, the flanges 38 need not be in contact with the bone screws 22 but are positioned such that if the bone screws 22 start to back out they will come into contact with the flanges 38 and thus be held in place. The base portion 26 is preferably configured to have at least two flanges 38 which are positioned around the base portion 26 so as to selectively permit passage of a bone screw 22 through a bone screw portal 14 and then, after the bone screw 22 is fully secured to the bone and seated in the bone screw portal 14 of the vertebral plate 12, the base portion 26 can be rotated to simultaneously lock at least two of the bone screws 22 to the vertebral plate 12.

The flanges 38 of the base portion 26 are positioned so as to be capable of lockably restraining or restricting the backing out of the bone screws at respective locking contact points 42, which are located beneath the head portions 40 of the screws 22. The locking mechanism being embedded in the underside 18 of the vertebral plate 12 and the locking contact points 42 being beneath the head of the bone screws 22, provides a substantially smooth top side 16 as compared to that of conventional plates. The upper surface 44 of the radially extending flanges of the lock can be provided with an integrally formed upward projection that serves as a locked position indicator 46 that is sized and configured to releasably fit into a receiving slot 48 defined through the body of the vertebral plate 12. Thus, when the bone screws 22 are passed through the bone screw portals 14 of the vertebral plate 12 and are threadably engaged with the underlying bone material, the locking tool (not shown) can be manually placed in the lock driving element 34, which is exposed on the top side 16 of the vertebral plate 12. As best shown in FIGS. 4A-B and 5A-B, the lock driving element 34 can be configured to have six inwardly projecting contacts 60 with six alternating projection recesses 62 for operationally receiving a standard locking tool having six radially directed rib-like projections. The manual rotation of the locking tool transmits the rotational torque to the locking mechanism 36. This torque force transfer effects the rotational movement of the embedded locking mechanism 36 within the vertebral plate 12, thus moving the flanges 38 from an unlocked position, which allows free movement of the bone screws through the bone screw portals, to a locked position wherein the radially extending flanges 38 of the base portion 26 become releasably engaged and thus prevent the removal or unintended backing out of the adjacent bone screws 22. When the flanges 38 are in the locked position with the bone screws 22, the upward projection on the flange 38, the locked position indicator 46, is aligned with the receiving slot 48. The locked position indicator 46 can be biased to snap into the space provided in the receiving slot 48 so as to give a visible indiction to the user that the locking mechanism 36 has been properly rotated into a locked position.

Importantly, the embedded locking mechanism 36 can be factory assembled and installed with only the lock driving element 34 exposed at the top side 16 of the vertebral plate 12. This design provides a low profile and a substantially smoother top side 16 surface as compared to having various additional locking components attached to the top side of conventional plate devices. The importance of maintaining the lowest possible profile and the smoothest possible top side 16 contact surface for adjacent soft tissue in the design of an anterior vertebral (and particularly cervical) plate is an obvious concern to those practicing in the art of spinal fixation and stabilization. Further, the novel design of the present invention, which embeds the locking mechanism 36 within the lock recess 24 on the underside 18 of the vertebral plate 12 (between the plate 12 and the bone) eliminates the possibility of components or elements of the vertebral plate 12 coming loose over time and migrating into surrounding soft tissues adjacent to the top side 16 of the vertebral plate 12. The possibility of such a mishap is unfortunately an ever present concern in the use of conventional plate devices that have locking components that are attached to the top side of the plate.

Figure 12:
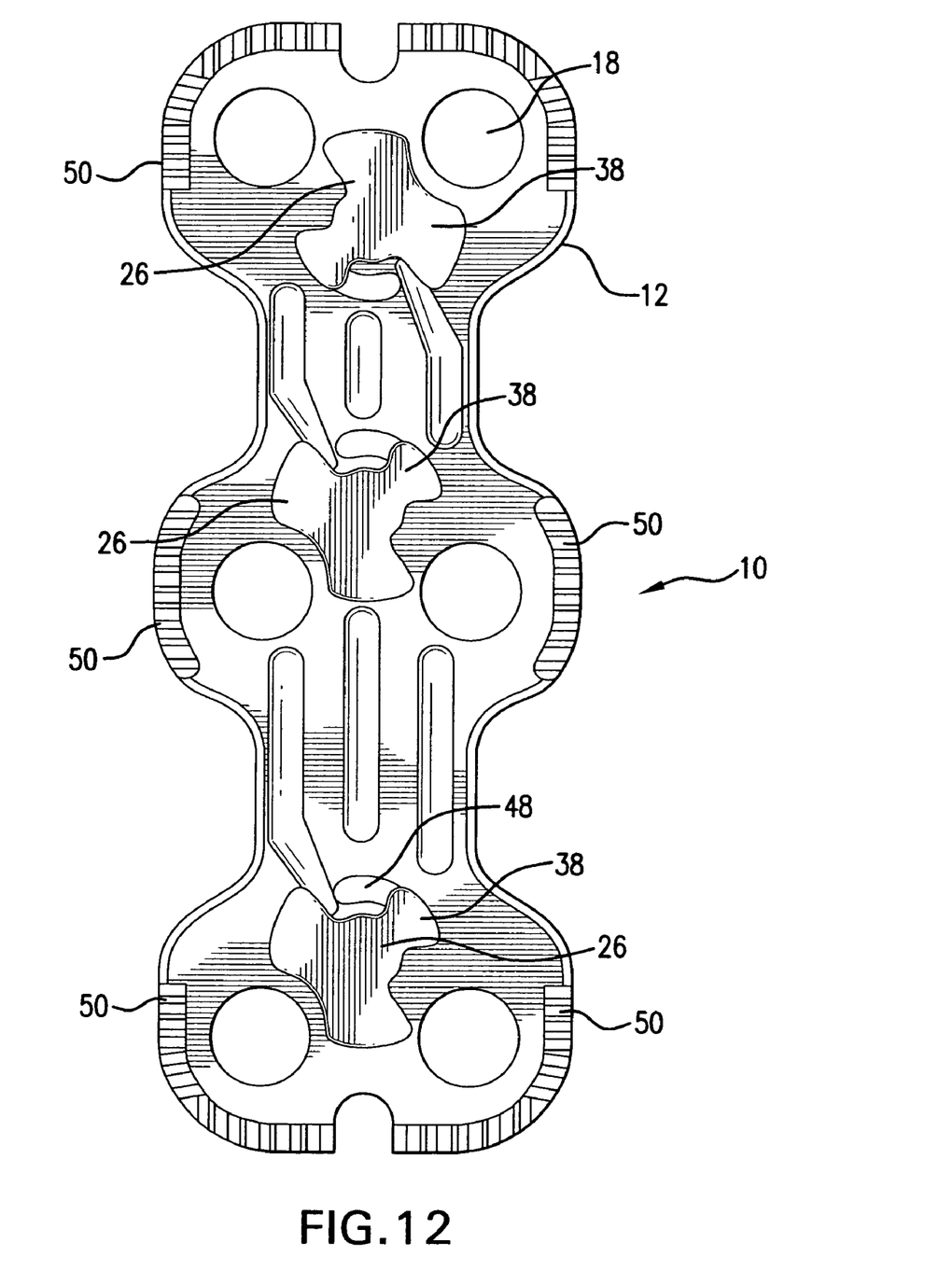
FIG. 12 shows an underside view of an alternative embodiment of the vertebral plate of the present invention having serrated feet selectively positioned at portions of the plate periphery as bone contact points from the plate body to the underlying bone.
Figure 13:
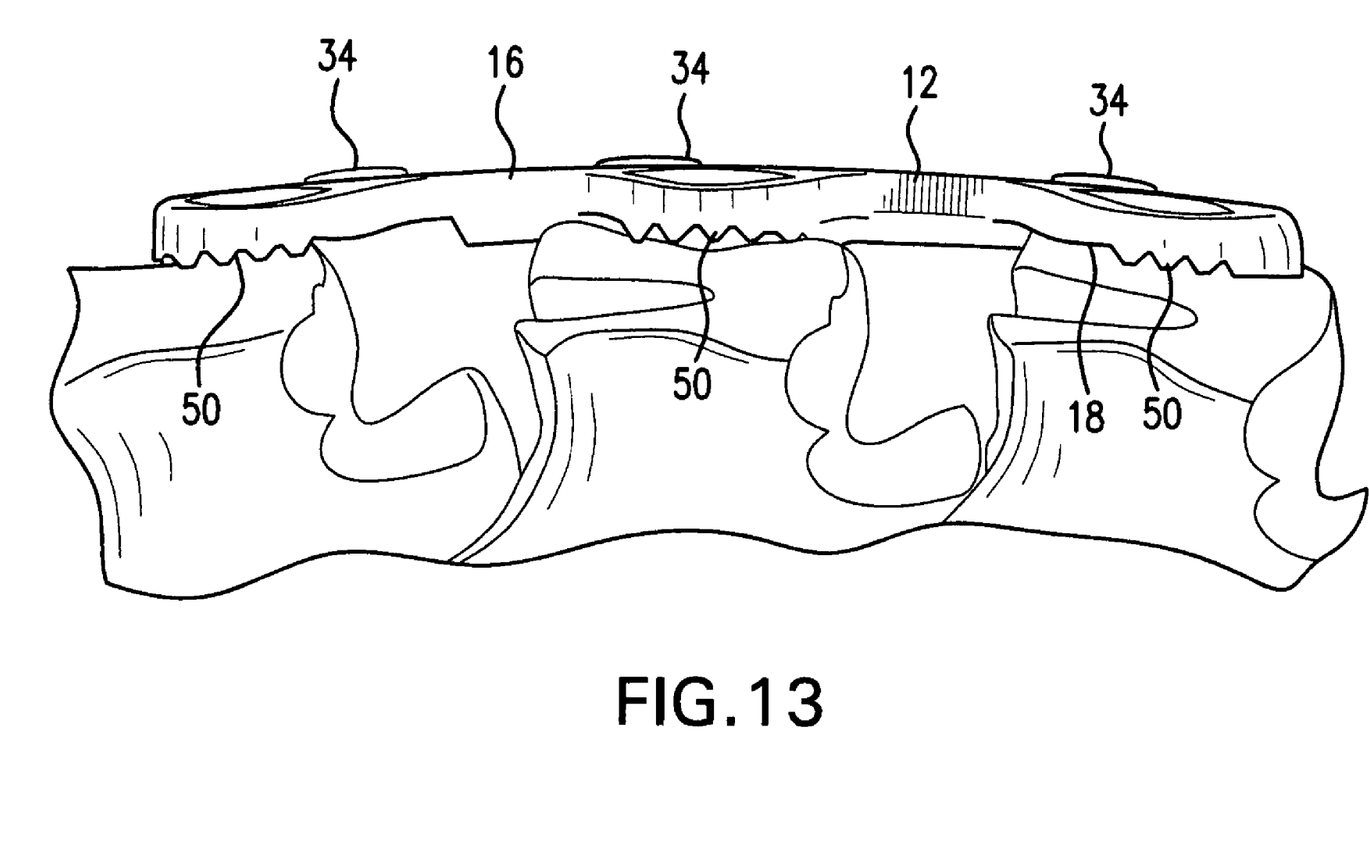
FIG. 13 shows a lateral view of a 2-level configuration of the alternative embodiment shown in FIG. 12, the vertebral plate being positioned on the anterior surface of the three vertebrae showing the contact of the serrated feet on the bone surface and the lack of contact of the underside of the plate to the bone.
Figure 14:
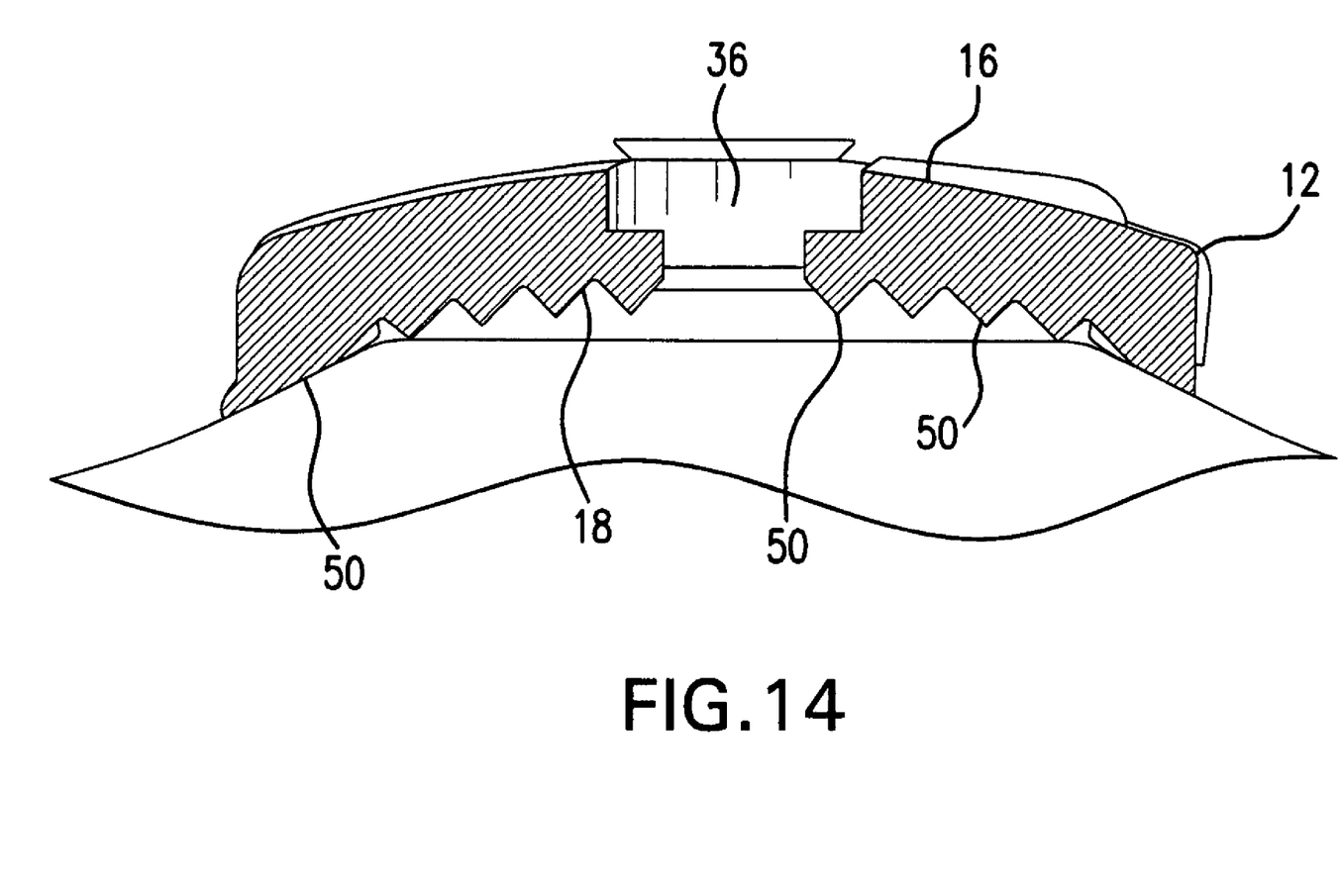
FIG. 14 shows a end view of the alternative embodiment shown in FIG. 12, wherein, due to the irregular surface of the bone, some of the serrated feed are in contact with the underlying bone and some of the serrated feet, like the underside of the vertebral plate are not in contact with the underlying bone.

As best shown in FIG. 12, an alternative embodiment of the present invention can be provided to include the additional element of downwardly directed bone contact points or feet 50, which are designed to make contact with the bone to which the plate is to be attached. The bone contacting surface of the feet 50 can be textured, ribbed, serrated, or in any other manner modified to increase the gripping ability of the surface. The inclusion of feet 50, as best shown in FIGS. 12-14, eliminates direct contact of the vertebral plate 12 to the underlying bone. The feet 50 are positioned around at least a portion of the perimeter of the vertebral plate 12 and preferably at the widest portion of the vertebral plate 12 as well as at the levels adjacent to where the bone screw portals 14 are located. As best shown in FIGS. 13-14, the alternative embodiment of the vertebral plate 12 facilitates the strength of attachment to the underlying bone and is particularly helpful in cases where the underlying bone has a very irregular surface. Importantly, the underside 18 of the vertebral plate 12 does not make contact with the bone and thus the problems that are sometimes associated with vertebral plates such as load transfer and stress shielding with resultant bone loss around the position of bone screw insertion can be avoided. The care in placement of the feet 50 at selected strategic points along the underside 18 of the vertebral plate 12 is very important to this avoidance of vertebral plate underside 18 surface contact with the underlying bone.

Figure 1A:
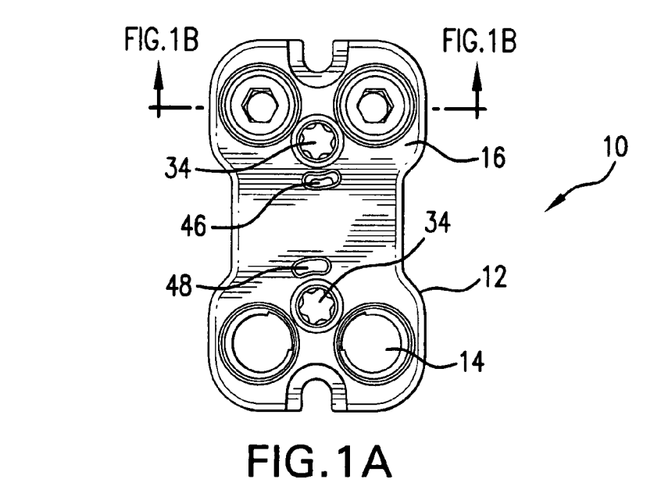
FIGS. 1A-C respectively show a top, front-cross-sectional, and underside oblique view of a vertebral plate system having two bone screws locked into the plate according to the present invention.
Figure 1B:
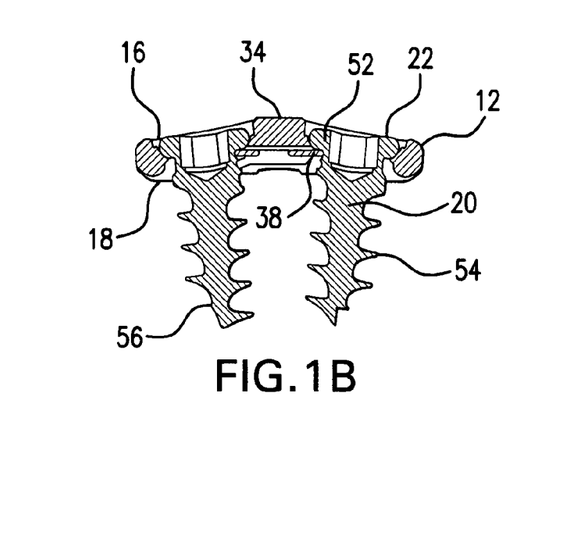
Figure 1C:
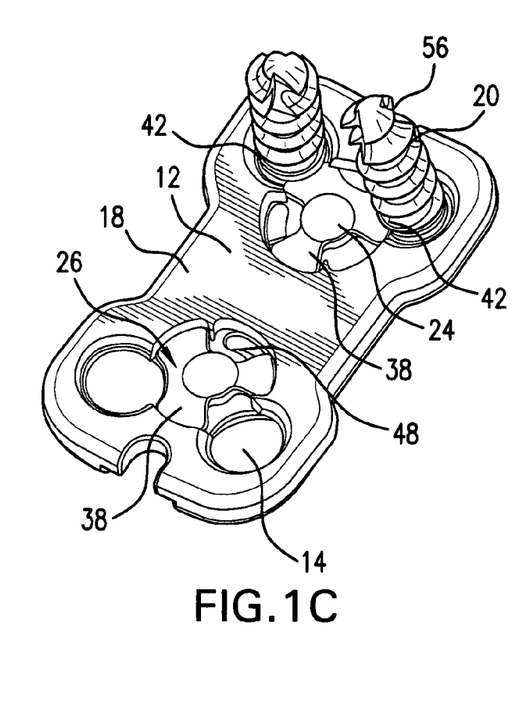
Figures 2A, 2B, 3A, 3B:
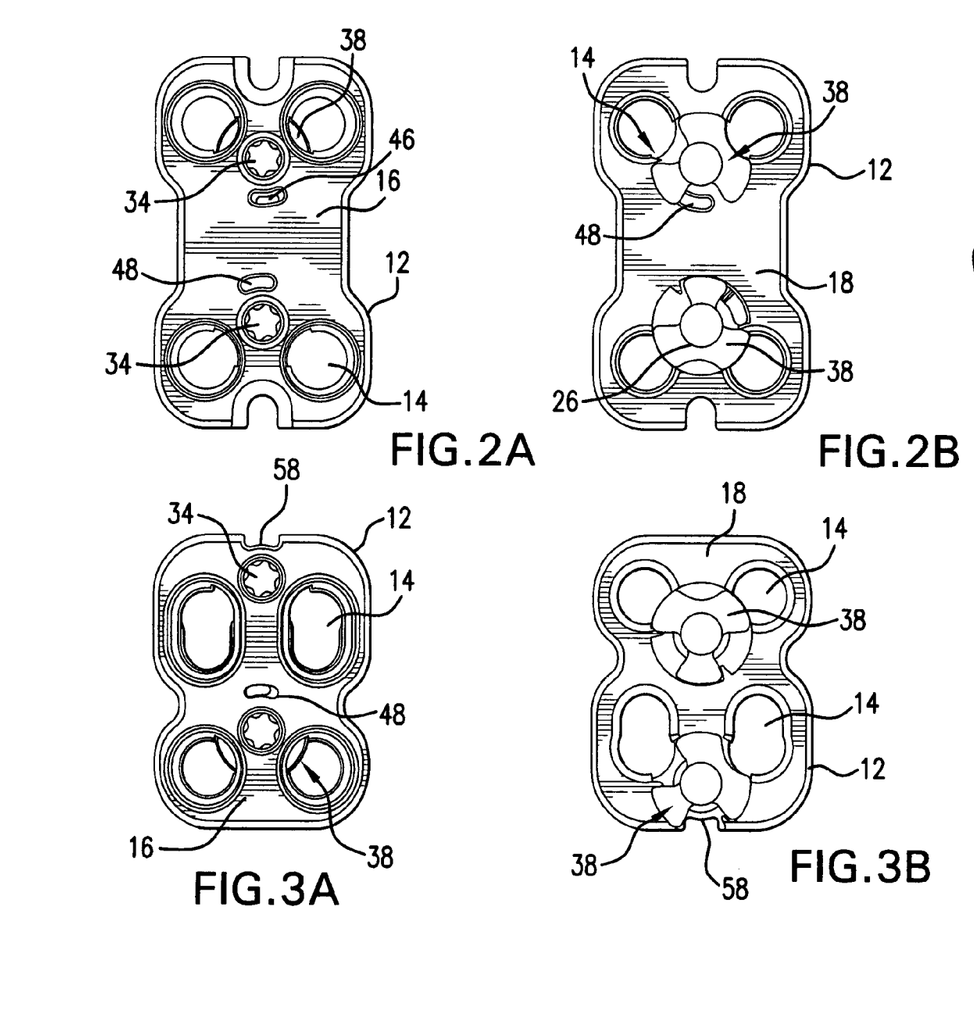
FIGS. 2A-C respectively show a top, underside, and top oblique view of a vertebral plate according to the present invention.
FIGS. 3A-C respectively show a top, underside, and top oblique view of a vertebral plate having bone screw portals including both circular-shaped holes and slots for receiving bone screws according to the present invention.
Figure 2C:
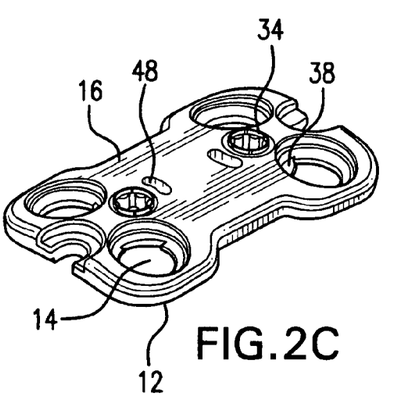
Figure 3C:
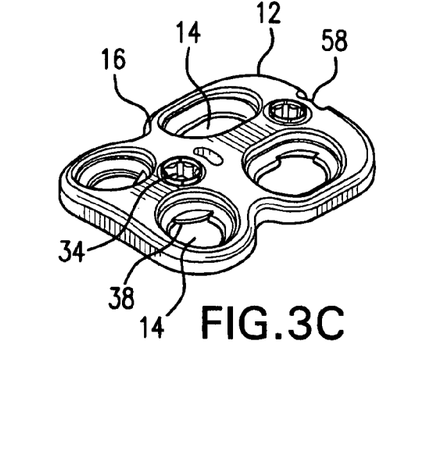
Figure 4A:
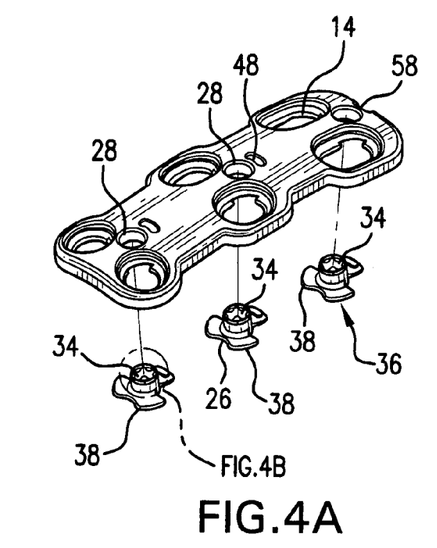
FIGS. 4A-B respectively show a top oblique exploded view of the vertebral plate embodiment having bone screw portals of varied configurations and sizes and a detailed magnified view of the lock driving element of the locking mechanism according to the present invention.
Figure 4B:
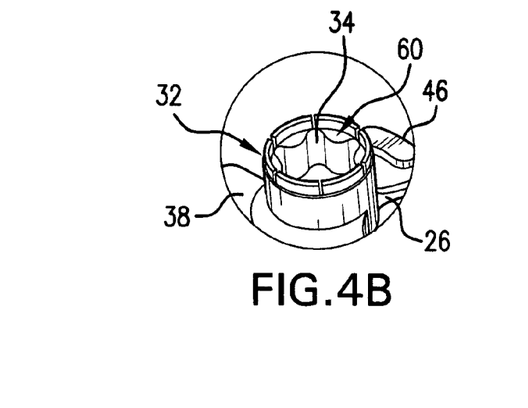
Figure 5A:
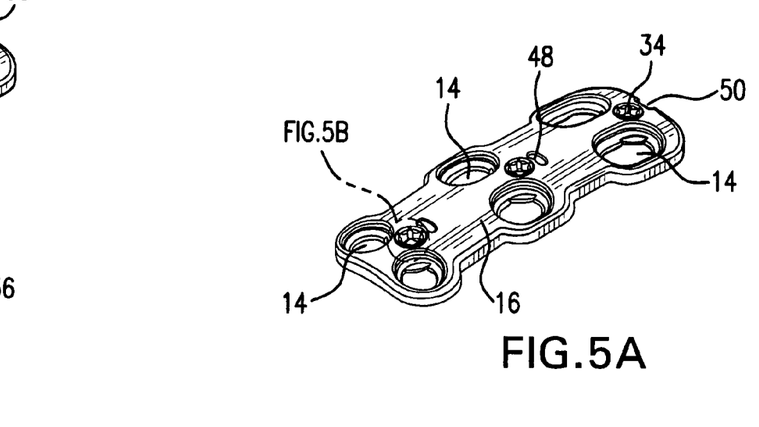
FIGS. 5A-B respectively show a top oblique assembled view of the vertebral plate embodiment having bone screw portals of varied configurations and sizes and a detailed magnified view of the lock driving element of the locking mechanism according to the present invention.
Figure 5B:
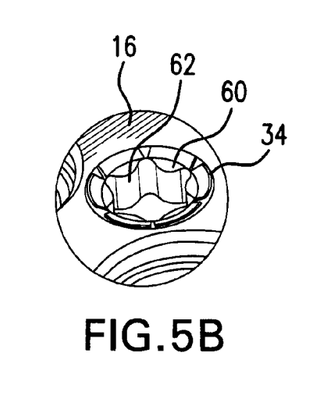
Figure 6A:
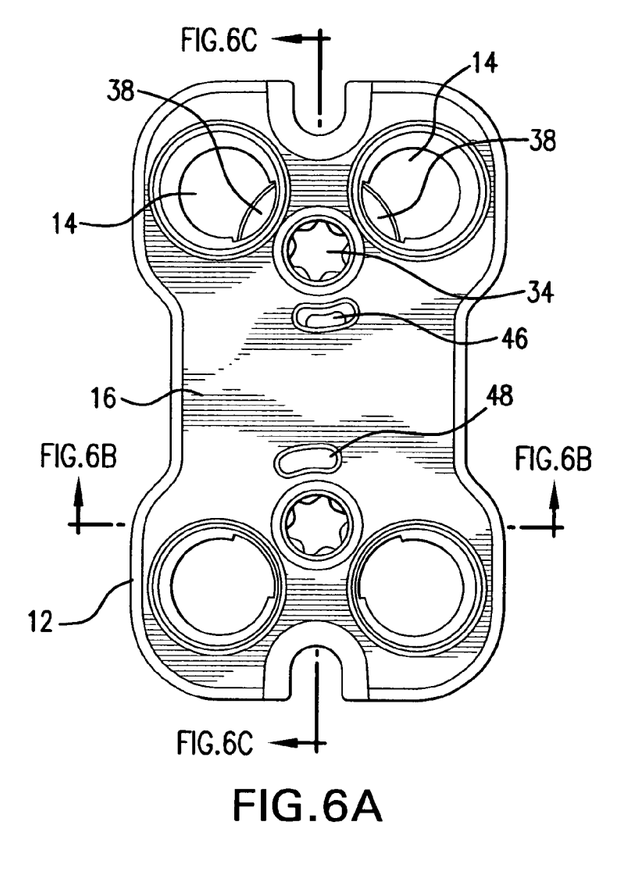
FIGS. 6A-C respectively show a top, front-cross-sectional, and side-cross sectional view of the vertebral plate embodiment of the present invention having circular bone screw portals according to the present invention.
Figure 6B:
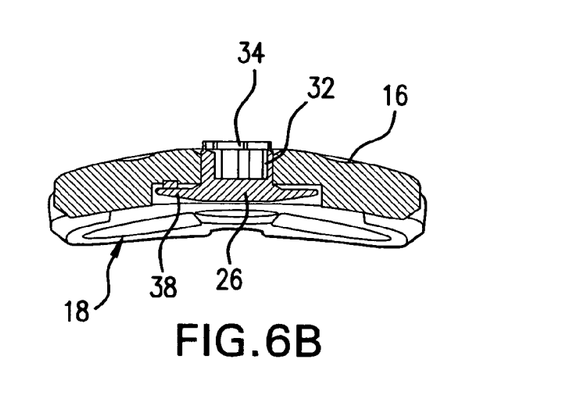
Figure 6C:
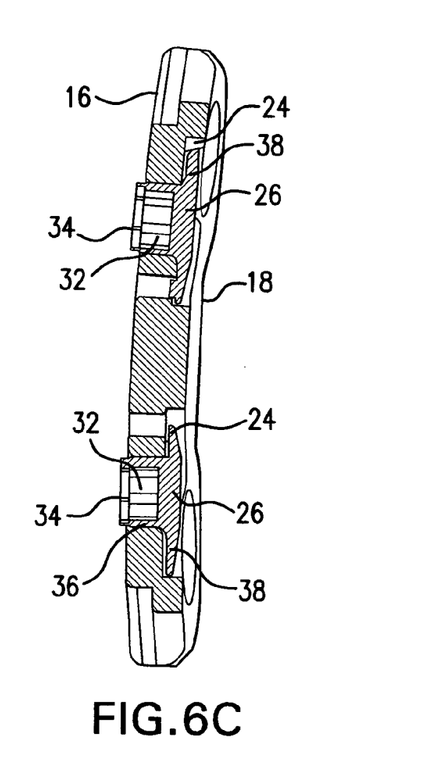
Figure 7A:
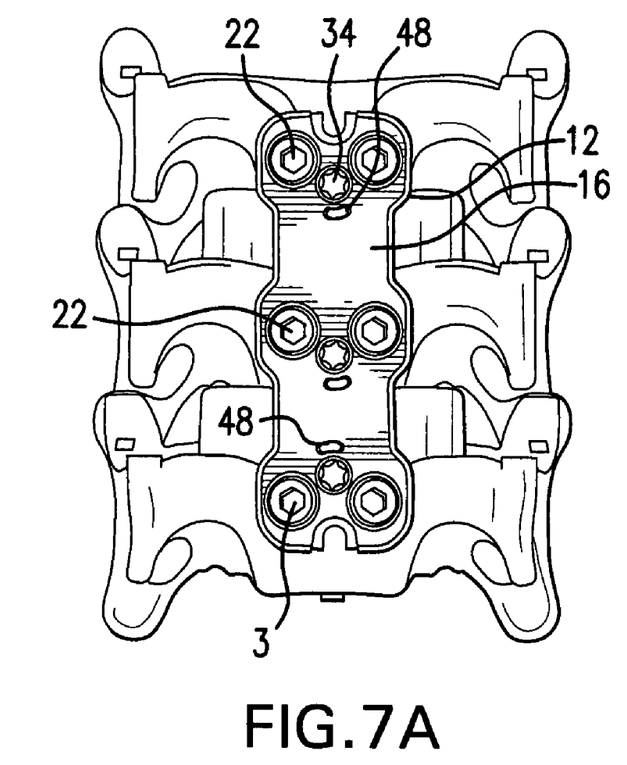
FIGS. 7A-B respectively show a top view of a 2-level embodiment of the present invention secured to a spine and a 1-level embodiment of the present invention secured to a spine.
Figure 7B:
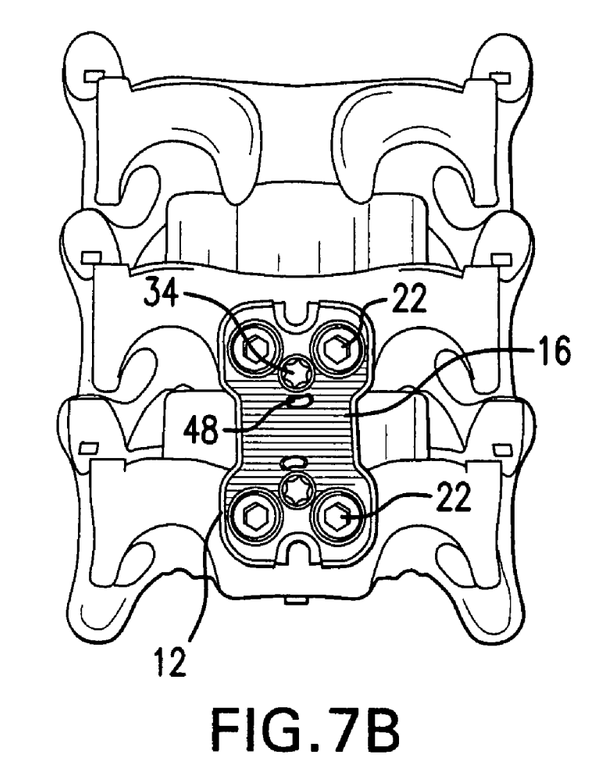
Figure 11:
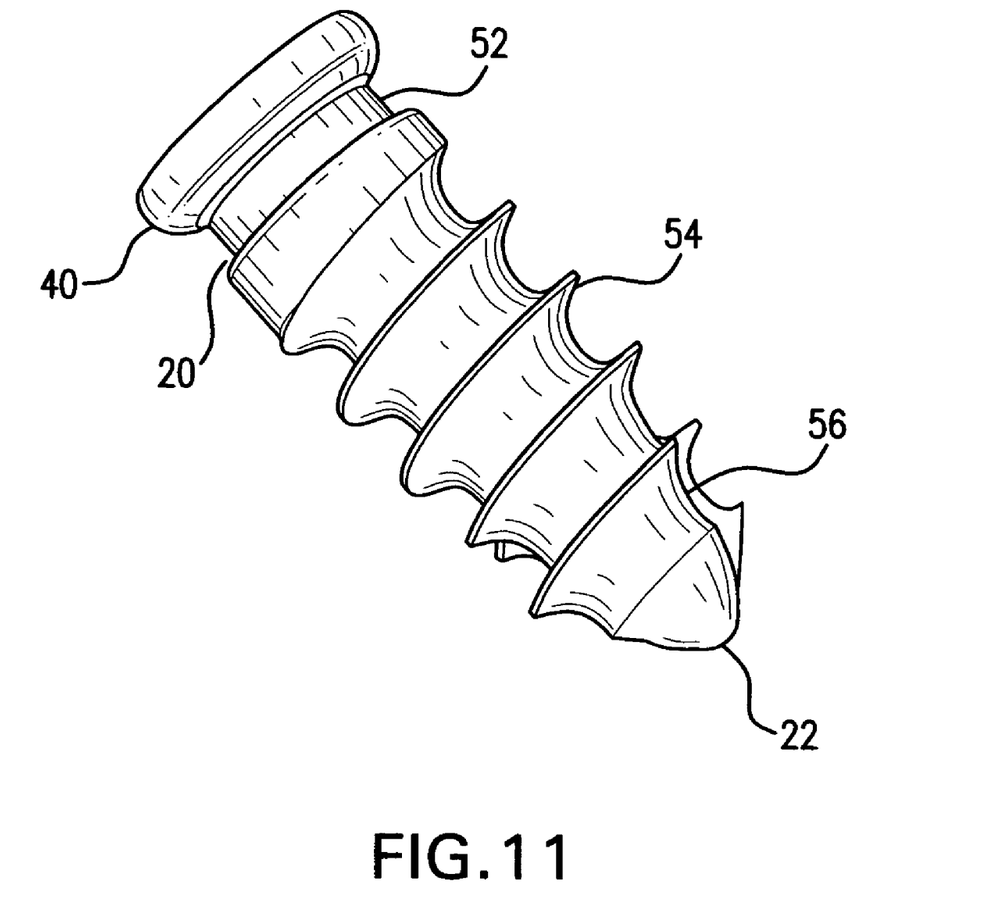
FIG. 11 shows an enlarged isomeric view of one embodiment of a bone screw that can be used with the vertebral plate of the present invention.

As best shown in FIG. 1B, FIG. 10 and FIG. 11, the head portion 40 of the bone screw 22 can be preferably provided as a flat head so as to be flush mounted with the surface plane of the top side 16 of the vertebral plate 12 when the bone screw 22 is fully installed in the plate 12 and screwed into the underlying bone. Preferably, the underside of the head portion 40 is rounded to permit an adjustable fit to the sides of the bone screw portal 14. The bone screw 22 can be provided with an undercut diameter 52 that is sized and configured to articulate and lock with the flanges 38 when the locking mechanism 36 is rotated into the locked position. The bone screws 22 used with the present invention can have standard bone threads 54 and self-tapping flutes 56.

The bone screws 22 can be used with vertebral plates having a variety of bone screw portals 14 to include holes or slots of varying length (i.e., L1, L2) as shown in FIGS. 2A-C, 3A-C, 4A-B, 5A-B, and 8A-C. Vertebral plates 12 employing such slots of varying length allow the vertebra to subside as compared to a screw hole, which doesn't allow subsidence.

As shown in all figures of the vertebral plate 12, the length and shape of the plate can be varied as needed to properly fit the anatomical needs of the subject without departing from the concept of the invention. The system 10 of the present invention can provide a plurality of vertebral plates 12 and screws 22 from which the surgeon can select as appropriate to the subject's needs. FIGS. 9C-F show various views of a preferred locking mechanism 36 as well as details of the lock operating shaft 32; however, it is within the concept of the present invention that the general geometry of the base portion 26 can vary from the preferred round geometry to hexagonal, octogonal, or other geometries. The number of flanges 38 on the base portion 26 can also be varied from that described herein. It is also possible to vary the configuration of the drive mechanism in the locking mechanism 36 to include, for example, various sizes of hexagon, square, hexalobular, slotted, cruciate and Phillips designs.

Standard bone screws or specially machined bone screws, such as those having an undercut diameter 52 for interacting with the flanges 38 of the locking mechanism 36 can be employed with the vertebral plate 12 of the present invention. The diameter of the bone screws 22 preferably can range from 2 mm to 9 mm with lengths ranging from 5 mm to 120 mm. The bone screws can also be cannulated without departing from the concept of the invention.

A kit can be provided to include a plurality of vertebral plates 12 and screws 22, as well as necessary instruments and tools for implanting the system 10 and locking the locking mechanism 36 of the vertebral plate 12. Instructions and packaging materials can also be included in such a kit. Such a kit can be provided in sterile packaging for opening and immediate use in the operating room.

The components of the present invention can be manufactured using methods and materials as known in the art such as for example, implant grade metallic materials, such as titanium, cobalt chromium alloys, stainless steel, and the like. It is also within the concept of the present invention that the components can be manufactured from any bio-compatible materials such as composite materials or plastics. Non-limiting examples of such materials include polyetheretherketone (PEEK) or polyaryletherketone (PAEK), or composites thereof, which can incorporate carbon fibers or similar materials. The materials used in the manufacture of the device and components of a kit can be radiopaque or radiolucent. The components of the present invention can be manufactured by any of a variety of known methods to include, for example, molding, casting, forming, machining, and extruding.

The method of the present invention provides for the implantation of the system of the present invention in a subject in need of the same. Variations of standard method steps in such surgical procedures can be made to adapt to the specific needs of the subject without departing from the concept of the invention. Normal operative techniques and tools for implantation of the device can be employed as necessary in accordance with safe surgical practices.

Each of the embodiments described above are provided for illustrative purposes only and it is within the concept of the present invention to include modifications and varying configurations without departing from the scope of the invention that is limited only by the claims included herewith. While the descriptive example of the present invention is primarily directed to fixation of cervical vertebrae, it is within the concept of the present invention to employ the system 10 and claimed method for the fixation of anterior lumbar or thoracic regions of the spine.

What is claimed is:

1. A spinal stabilization device, comprising:
a vertebral plate, said plate defining at least two bone screw portals and having a plate top side and a plate underside, the underside being disposed in opposition to the anterior surface of vertebral bone when said system is implanted in a subject, said vertebral plate further defining a receiving slot, said receiving slot being in communication with said cam recess and said top side of said vertebral plate, wherein said locked position indicator is visible through said receiving slot when said plurality of flanges have been rotated into a locked position;
a cam locking mechanism including a cam having a plurality of outwardly directed flanges, said flanges configured to directly engage locking contact points beneath the head of a bone screw disposed in one of said bone screw portals and lock in place said bone screw, said locking mechanism being embedded and rotatably attached within a cam recess defined in the underside of said vertebral plate, one of said plurality of flanges comprises an integrally formed upward extending projection that serves as a cam locked position indicator, wherein said cam is connected to a cam driver receptacle by an intermediately positioned cam operating shaft, said cam being rotatably positioned within said cam recess and said cam operating shaft being rotatably positioned within a cam shaft lumen, said cam shaft lumen being defined by said vertebral plate and providing a through passage from said cam recess in said plate underside to said top side of said vertebral plate, said cam being configured to selectively engage and lock in place bone screws when said bone screws are positioned within said bone screw portals and said cam has been rotated within said cam recess to a locked position.

2. The device of claim 1, wherein said cam locked position indicator is biased to snap upward into said receiving slot when said plurality of flanges are rotated into a locked position.

3. The device of claim 2, wherein said receiving slot is positioned adjacent to a peripheral edge of said vertebral plate so as to form an opened-sided notch in said vertebral plate.

4. The device of claim 1, wherein at least one of said bone screw portals is configured as a bone screw hole.

5. The device of claim 1, wherein at least one of said bone screw portals is configured as a bone screw slot.

6. The device of claim 5, wherein said at least two bone screw portals comprises at least two of said bone screw slots, at least two of said slots being of a different slot length from the other.

7. The device of claim 1, wherein said vertebral plate comprises selectively positioned feet, said feet being positioned at sections along the periphery of said vertebral plate and extending downward from said underside of said vertebral plate, said feet being configured to contact the surface of the bone of a subject so as to preclude the underside of the vertebral plate from making contact with any portion of the underlying bone when said device is implanted into a subject in need thereof.

8. A spinal stabilization system, comprising:
 a vertebral plate, said plate defining at least two bone screw portals and having a plate top side and a plate underside, the underside being opposed to the anterior surface of vertebral bone when said system is implanted in a subject, said vertebral plate further defining a receiving slot, said receiving slot being in communication with said cam recess and said top side of said vertebral plate, wherein said locked position indicator is visible through said receiving slot when said plurality of flanges have been rotated into a locked position;
 a cam locking mechanism including a cam having a plurality of outwardly directed flanges, said cam locking mechanism comprises a cam connected to a cam driver receptacle by an intermediately positioned cam operating shaft, said cam being rotatably positioned within said cam recess and said cam operating shaft being rotatably positioned within a cam shaft lumen, said cam shaft lumen being defined by said vertebral plate and providing a through passage from said cam recess in said plate underside to said top side of said vertebral plate, said flanges configured to directly engage locking contact points beneath the head of a bone screw and lock in place said bone screw, said cam locking mechanism being embedded and rotatably attached within a cam recess defined in the underside of said vertebral plate, wherein at least one of said flanges comprises an integrally formed upward extending projection that serves as a locked position indicator, wherein said cam further comprises a plurality of radially extending flanges configured to selectively engage and lock in place said at least two bone screws when said bone screws are positioned within said bone screw portals and said cam has been rotated within said cam recess to a locked position;
 at least two bone screws, each of said bone screws having a locking contact point beneath the head of said bone screws, each bone screw corresponding to and sized to pass partially through a respective bone screw portal of said at least two bone screw portals and configured so as to be selectively engaged at said locking contact point and locked into place by said cam locking mechanism, wherein said at least two bone screws each comprise a head portion, said head portion being of flat configuration so as to be at or below the surface plane level of said top side of said vertebral plate when said bone screws are fully engaged in said vertebral plate.

9. The system of claim 8, wherein said locked position indicator is biased to snap upward into said receiving slot when said plurality of flanges are rotated into a locked position.

10. The system of claim 8, wherein said receiving slot is positioned adjacent to a peripheral edge of said vertebra plate so as to form an opened-sided notch in said vertebral plate.

11. The system of claim 8, wherein said contact points being inwardly directed undercuts that are circumferentially defined on the shank of said bone screws at a point adjacent to the undersurface of said head of said bone screw, said undercut on said bone screws being sized and configured to engage with one of said flanges when said flange is selectively rotated to a cam locked position.

12. The system of claim 8, wherein said at least two bone screws are self-tapping screws.

13. A method of fixation of the spine of a subject, comprising:
 determining that a subject is in need of or potentially in need of a procedure to implant the device of claim 1; and
 connecting the device of claim 1 to any existing construct on an adjacent level.

14. A kit for use in a surgical procedure, said kit comprising:
 at least two or more devices according to claim 1, wherein said two or more devices comprise devices of different sizes and configurations, said different configurations including at least one device selected from the group consisting of devices having bone screw holes of generally circular shave, devices having bone screw slots of varying slot lengths, devices having both bone screw holes and bone screw slots, devices having receiving slots for visually determining when said cam is in a locked position; and devices having receiving notches for visually determining when said cam is in a locked position;
 a locking tool configured to operably engage said cam driving element; and
 a sealable packaging container for said kit.

* * * * *